(12) United States Patent
Franzke et al.

(10) Patent No.: US 8,871,965 B2
(45) Date of Patent: Oct. 28, 2014

(54) METHOD FOR PRODUCING URETHANES

(75) Inventors: Axel Franzke, Mannheim (DE); Robert Baumann, Mannheim (DE); Michael Bock, Ruppertsberg (DE)

(73) Assignee: BASF SE, Ludwigshafen (DE)

( * ) Notice: Subject to any disclaimer, the term of this patent is extended or adjusted under 35 U.S.C. 154(b) by 21 days.

(21) Appl. No.: 13/501,621

(22) PCT Filed: Oct. 20, 2010

(86) PCT No.: PCT/EP2010/065765
§ 371 (c)(1),
(2), (4) Date: Apr. 12, 2012

(87) PCT Pub. No.: WO2011/048124
PCT Pub. Date: Apr. 28, 2011

(65) Prior Publication Data
US 2012/0203022 A1 Aug. 9, 2012

(30) Foreign Application Priority Data

Oct. 21, 2009 (EP) .................................... 09173667

(51) Int. Cl.
*C07C 271/06* (2006.01)
*C07C 263/04* (2006.01)
*C07C 269/04* (2006.01)

(52) U.S. Cl.
CPC ............. *C07C 269/04* (2013.01); *C07C 263/04* (2013.01)
USPC ......................................................... 560/24

(58) Field of Classification Search
USPC ....................... 560/24, 33, 338, 345
See application file for complete search history.

(56) References Cited

U.S. PATENT DOCUMENTS

| | | | |
|---|---|---|---|
| 3,763,217 A | 10/1973 | Brill | |
| 4,268,683 A | 5/1981 | Gurgiolo | |
| 4,268,684 A | 5/1981 | Gurgiolo | |
| 4,395,565 A | 7/1983 | Romano et al. | |
| 4,550,188 A | 10/1985 | Frulla et al. | |
| 5,773,643 A * | 6/1998 | Yagii et al. .................... | 560/345 |
| 2010/0331564 A1 | 12/2010 | Leitner et al. | |
| 2011/0004012 A1 | 1/2011 | Leitner et al. | |
| 2011/0015424 A1 | 1/2011 | Leitner et al. | |
| 2011/0137067 A1 | 6/2011 | Franzke et al. | |
| 2011/0313192 A1 | 12/2011 | Rosendahl et al. | |
| 2012/0101299 A1 | 4/2012 | Schelling et al. | |

FOREIGN PATENT DOCUMENTS

| | | |
|---|---|---|
| DE | 32 02 690 | 3/1984 |
| EP | 0 048 371 | 3/1982 |
| EP | 0 391 473 | 10/1990 |
| WO | 98 55450 | 12/1998 |
| WO | 98 55451 | 12/1998 |
| WO | WO9947493 * | 9/1999 |
| WO | 01 68590 | 9/2001 |
| WO | 2007 015852 | 2/2007 |
| WO | 2008 084842 | 7/2008 |
| WO | 2009 115537 | 9/2009 |
| WO | 2009 115538 | 9/2009 |
| WO | 2009 115539 | 9/2009 |
| WO | WO2009115538 A1 * | 9/2009 |
| WO | 2010 020621 | 2/2010 |
| WO | 2010 149544 | 12/2010 |

OTHER PUBLICATIONS

Leitner et al. (WO 2009/115538 A1), English translation of the description/claims were conducted on the website titled Espacenet on Jul. 23, 2013 and Jul. 8, 2013 respectively.*
Tundo et al. (Dimethyl Carbonate as an Ambident Electrophile, Journal of Organic Chemistry, vol. 70, pp. 2219-2224, Published on web Feb. 17, 2005).*
Leitner et al. (WO 2009/115538 A1).The English translation of the description and claims was conducted on the website titled Espacenet on Jul. 23, 2013 and Jul. 8, 2013 respectively.*
Tundo et al. (Dimethyl Carbonate as an Ambident Electrophile, Journal of Organic Chemistry, vol. 70, pp. 2219-2224, Published on web Feb. 17, 2005).*
Baba, T., et al., "Characteristics of methoxycarbonylation or aromatic diamine with dimethyl carbonate to dicarbonate using a zinc acetate catalyst," Green Chemistry, vol. 7, pp. 159-165, (Jan. 18, 2005).
Tundo, P., et al., "Dimethyl Carbonate as an Ambident Electrophile," Journal of Organic Chemistry, vol. 70, pp. 2219-2224, (2005).
International Search Report Issued on Feb. 16, 2011 in PCT/EP10/65765 Filed Oct. 20, 2010.

* cited by examiner

*Primary Examiner* — Brandon Fetterolf
*Assistant Examiner* — Blaine G Doletski
(74) *Attorney, Agent, or Firm* — Oblon, Spivak, McClelland, Maier & Neustadt, L.L.P.

(57) ABSTRACT

The content of the invention is a process for preparing urethanes by reaction of aromatic amines with a dialkyl carbonate, wherein the alkyl radical of the organic dialkyl carbonate comprises 4-18 carbon atoms and is branched in the 2 position, and the reaction is performed in the presence of a substoichiometric amount of base, based on the amino groups.

20 Claims, 1 Drawing Sheet

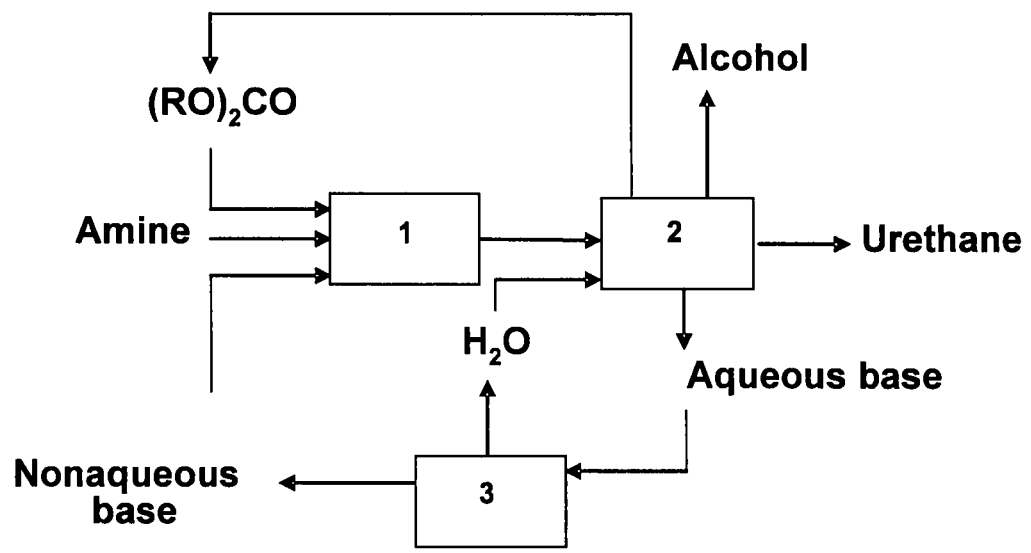

METHOD FOR PRODUCING URETHANES

CROSS REFERENCE TO RELATED APPLICATION

This application is a 371 of PCT/EP2010/065765, filed on Oct. 20, 2010, and claims priority to European Patent Application No. 09173667.8, filed on Oct. 21, 2009.

The invention provides a process for preparing urethanes by reaction of mono-, di- or polyfunctional aromatic amines with a dialkyl carbonate in the presence of a base. The urethanes thus prepared can subsequently be converted to industrially important isocyanates.

For preparation of urethanes, also known as carbamates, a number of different processes are known. In the reactions, Lewis acids, for example aluminum turnings, are used with iodine and mercury promoters (U.S. Pat. No. 4,550,188), and also uranium salts, zinc salts, iron salts, titanium salts, lead salts, zirconium salts, antimony salts, cobalt salts, scandium salts or tin salts as catalysts, as described, for example, in U.S. Pat. No. 3,763,217, U.S. Pat. No. 4,268,683 or U.S. Pat. No. 4,268,684. Disadvantages for the industrial use of these processes are the long reaction times, low conversions, low selectivities or several features together.

High yields are obtained in these processes catalyzed by Lewis acids in the case of use of lead salts or zinc salts when a high excess of dimethyl carbonate is used, preferably a ratio of amine to carbonate of at least 1:12, as described, for example, in WO 98/55450, WO 98/55451, WO 01/68590 or Green Chemistry 2005, 7, 159-165. The high excess of dimethyl carbonate leads to large recycle streams and/or losses of this reagent.

In other cases, high yields of carbamates can be achieved when the urea likewise formed in the urethanization is converted thermally in an additional reaction to the corresponding urethane, for example using lead catalysts, titanium catalysts, zinc catalysts and zirconium catalysts, as described in EP 0048371 and EP 0391473. This requires an additional, energy-intensive step.

A further general disadvantage in the case of use of Lewis acids as homogeneous catalysts is the catalyst residues which remain in the product, the removal of which is incomplete and/or complex. To avoid these problems, WO 2007/015852 describes the use of Lewis-acidic heterogeneous catalysts for the urethanization of aromatic amines. This simplifies the removal of the pure product considerably, but the conversions obtained are too low for an industrial scale use and, together with the selectivities, decrease with increasing service life of the heterogeneous catalyst.

It is additionally known that aromatic amines can be converted to the corresponding urethanes using basic compounds, for example alkali metal or alkaline earth metal alkoxides. DE 3202690 describes the reaction of aniline with dialkyl carbonates in the presence of small amounts of metal alkoxides as catalysts. The conversions described in the examples are incomplete and the selectivities achieved are insufficient for industrial use.

Journal of Organic Chemistry 2005, 70, 2219-2224 describes the reaction of aniline with a 40-fold excess of dimethyl carbonate in the presence of a superstoichiometric amount of bases such as sodium methoxide (NaOMe) or potassium tert-butoxide (KOtBu). With NaOMe, a selectivity of 67% after 210 min of reaction time is obtained. With KOtBu, a selectivity of 100% is measured after 1 min, but this declines to 60% with increasing reaction time as a result of formation of the N-methylcarbanilate by-product. Conversions and isolated yields are not described.

Finally, WO 2008/084842 describes the preparation of aromatic carbamates using small excesses of dialkyl carbonates (2.5 to 3 equivalents based on amino groups) and catalytic amounts of sodium methoxide, and the further conversion thereof to the corresponding isocyanates. However, no figures are given for the reaction times needed for this purpose, and yields after the urethanization.

WO 2009/115538 discloses the reaction of aromatic diamines with only small excesses, namely two equivalents per amino group, of dialkyl carbonates of higher alcohols having at least two carbon atoms in the chain, in the presence of stoichiometric amounts of alkali metal alkoxides, which enables high isolated yields of carbamates. However, the recycling of such large amounts of base means a large expenditure of energy, which lowers the economic viability of this process to a high degree.

In addition, WO 2010/020621 also describes a similar preparation of carbamates using only catalytic amounts of base. However, the carbonates which derive from alcohols comprising heteroatoms and are required for this purpose are difficult to synthesize and hence are only of limited availability.

It was an object of the invention to develop an industrially performable process for preparing urethanes from mono-, di- or polyfunctional aromatic amines, which leads to high space-time yields and selectivities. The process was to be possible using dialkyl carbonates obtainable on the industrial scale. At the same time, small molar excesses of dialkyl carbonates, based on the amino groups, were to be employed. In addition, the amount of the base used was to be at a minimum. The urethanes obtained in this way are subsequently to be processed to give aromatic isocyanates of industrial importance.

It has been found that, surprisingly, the reaction of aromatic amines with dialkyl carbonates whose primary alkyl radicals have a branch in the 2 position, in the case of low carbonate excesses, even in the presence of substoichiometric amounts of a base, allows isolation of the desired urethanes in very good yields of up to 97%. In addition, a very good selectivity was achievable as a result.

The invention accordingly provides a process for preparing urethanes by reaction of aromatic amines with a dialkyl carbonate, wherein the alkyl radical of the organic dialkyl carbonate comprises 4-18 carbon atoms, preferably 4-10 carbon atoms, and is branched in the 2 position, and the reaction is performed in the presence of a substoichiometric amount of base, based on the amino groups.

The reaction product of the aromatic amine and the dialkyl carbonate is preferably reacted with a protic compound. A protic compound is understood to mean a compound which can transfer a proton. The protic compound is preferably selected from a group comprising alcohols, water and mixtures of the two. Particular preference is given to the use of water.

The base is used preferably in a molar ratio of 0.3 to less than 0.8, based on the amino groups, more preferably of 0.4 to 0.6 based on the amino groups.

The dialkyl carbonate is preferably used in a molar ratio of dialkyl carbonate to amino groups of 1:1 to 6:1, more preferably of 1:1 to 3:1.

The reaction of the aromatic amine with the dialkyl carbonate in the presence of the base is performed preferably at a reaction temperature of 60-180° C., more preferably of 100-150° C. At this temperature, a quantitative conversion of the aromatic amine is obtained within 0.5-10 h. The reaction is performed typically at standard pressure, or else under (autogenous) elevated pressure or reduced pressure. In this case, the alcohol formed can be left in the reaction mixture or distilled off. In one embodiment of the invention, the reaction is performed in the presence of an inert solvent. Suitable solvents are, for example, mono- or polyethers, such as dioxane, diphenyl ether or dibenzyl ether, and dialkyl ethylene glycols, such as diethylene glycol dimethyl ether, diethylene glycol dibutyl ether or triethylene glycol dimethyl ether, aromatic hydrocarbons with or without alkyl, halogen or alkoxy substituents, such as toluene, the isomeric xylenes, mesitylene, ethylbenzene, tetralin, the isomeric benzyl- and dibenzyltoluenes, chlorobenzene, the isomeric dichloro- and trichlorobenzenes or anisole, or the alcohol present in the dialkyl carbonate and/or alkoxide. These can be used individually or as a mixture.

In the process according to the invention, mono-, di- or polyfunctional aromatic amines are used. The aromatic amines preferably do not comprise any heteroatoms in the aromatic radical. Representatives from this group are, for example, aniline, o-, m-, p-toluidine and mixtures thereof, o-, m-, p-chloroaniline and mixtures thereof, o-, m-, p-bromoaniline and mixtures thereof, o-, m-, p-trifluoromethylaniline and mixtures thereof, 2,4-, 2,6-, 3,4- and 3,5-dimethyl-, -dichloro-, -dibromo- and -diethylaniline and isomer mixtures thereof, p-tert-butylaniline, diaminotoluene (TDA), especially 2,4- and 2,6-diaminotoluene and mixtures thereof, diaminodiphenylmethane (MDA), especially 2,4'-diaminodiphenylmethane, 4,4'-diaminodiphenylmethane, 2,2"-diaminodiphenylmethane and higher homologs (polyphenylenepolymethylenepolyamines) and mixtures thereof, and o-, m-, p-phenylenediamine and mixtures thereof. Preference is given to using aniline, the isomers of diaminotoluene and the isomers and higher homologs of diaminodiphenylmethane.

The alkyl chain of the dialkyl carbonate comprises 4-18 and preferably 4-10 carbon atoms, and is branched in the 2 position. It derives from the corresponding primary alcohol. The alkyl chain may additionally also comprise saturated or unsaturated rings. In one embodiment of the invention, the alkyl chain of the dialkyl carbonate has been modified with an oxygen atom. This is preferably in the form of an ether group.

In a particularly preferred embodiment of the invention, the dialkyl carbonates are selected from the group comprising di(2-methylpropyl) carbonate, di(2-methoxypropyl) carbonate, di(2-ethoxypropyl) carbonate, di(2-methylbutyl) carbonate, di(2-ethylhexyl) carbonate, di(cyclopentylmethyl) carbonate and di(cyclohexylmethyl) carbonate, preferably di(2-methylpropyl) carbonate and di(2-methoxypropyl) carbonate, more preferably di(2-methylpropyl) carbonate.

The dialkyl carbonate is preferably prepared by transesterification of an alkylene carbonate with an alcohol.

The base preferably comprises basic organic metal compounds, especially compounds or alkali metals. These compounds may, for example, be compounds comprising nitrogen atoms, for example amides such as sodium amide, or compounds comprising silicon atoms and nitrogen atoms, for example lithium hexamethyldisilazide. More preferably, the base is an alkoxide of alkali metals or alkaline earth metals.

The alkyl chain of the alkoxide is linear, branched or cyclic and comprises 1-18 and preferably 4-10 carbon atoms. The alcohol may additionally also comprise saturated or unsaturated rings. In one embodiment of the invention, the alkyl chain of the alkoxide has been modified by at least one oxygen atom. This is preferably in the form of an ether group.

In a particularly preferred embodiment of the process according to the invention, the dialkyl carbonates and the alkoxides are based on the same alcohol. This has the advantage that a smaller amount of compounds is present in the process according to the invention. This reduces the separation complexity within the process.

In a preferred embodiment of the process according to the invention for preparation of urethanes, in which water is used as the protic compound, the process according to the invention comprises the steps of a) reaction of an aromatic amine with the organic carbonate in the presence of a base
b) reaction of the reaction products from step a) with water
c) separation of the products formed in step b) and of the aqueous base
d) conversion of the aqueous base from step c) to the corresponding nonaqueous base and the recycling thereof into step a)
e) isolation of the urethane separated in step c).

This process is performed continuously or batchwise, preferably continuously. In this case, the urethane is formed in step b). This embodiment is shown in FIG. 1 for the use of water as the protic compound. The urethane can be isolated as a solution in an organic solvent or as a pure substance in the form of a melt or of a solid. The products formed in step b) comprise the urethane and, in the case of use of a sodium alkoxide as the base, sodium hydroxide solution.

Process step a) is performed in stage 1 of FIG. 1, process step b) in stage 2. In the case of a batchwise mode of operation stages 1 and 2 can be performed in the same reaction vessel, in the case of a continuous mode of operation preferably in different reaction vessels. The product from stage 1 can be transferred into stage 2 without further workup.

In stage 3, the aqueous base obtained in stage 2 is converted to the nonaqueous base, in the case of use of alkoxides the conversion of the hydroxide to the alkoxide. The latter is recycled into stage 1. Excess alcohol which is obtained in stage 2 is discharged there or recycled to another point in the process. The water formed in the course of formation of the base or of the alkoxide can be recycled back into step b). The aqueous alkali formed in step b) can be reacted with alcohol to give the corresponding alkoxide and the latter can be recycled back into step a).

The product from stage 2 is, if it is not already present in this form, separated into a nonaqueous phase and an aqueous phase. The product is removed from the organic phase comprising the urethane and isolated as a solid or melt, or used directly in this form in further reaction stages, for example a thermal cleavage to the corresponding isocyanate. The urethanes removed can, if necessary, be purified by means of methods familiar to the person skilled in the art, for example by washing with water or organic solvents, or recrystallization from a suitable solvent.

The thermal cleavage of the urethane to the corresponding isocyanate may directly follow step e) as step f).

The dialkyl carbonate used in step a) can preferably be prepared by transesterification of an alkylene carbonate with an alcohol.

In this invention, it has been shown that the inventive reaction of aromatic amines with a small excess of dialkyl carbonates derived from branched alcohols in the presence of substoichiometric amounts of a base to give the corresponding carbamates is possible in high selectivities and space-time yields. The urethanes are formed in high purities, and so typically no complex postpurification is required.

While the reaction of aromatic amines with low carbonate excesses in the presence of a stoichiometric amount of base, based on the amino groups, gives comparable isolated yields for a whole series of dialkyl carbonates, for example 90% or more for 2,4-diaminotoluene in WO 2009/115538, i.e. high conversions and high selectivities, the efficiency of the reactions decreases significantly in the case of use of a smaller amount of base.

If only about 0.5 equivalent of base is used, based on the amino groups, in the case of use of noninventive linear carbonates such as di-n-propyl carbonate or bis(2-methoxyethyl) carbonate, only distinctly reduced yields of not more than 84% are achieved for 2,4-diaminotoluene, i.e. high conversions at low selectivities. Only in the case of use of the inventive 2-branched carbonates such as diisobutyl carbonate do the high isolable yields not change, and 96% is achieved for 2,4-diaminotoluene, i.e. high conversions and high selectivities.

In the case of use of a much lower, catalytic amount of base (0.2 equivalent or less, based on amino groups), acceptable conversions are achieved only with carbonates which derive from alcohols comprising heteroatoms, such as bis(2-methoxyethyl) carbonate. However, in these cases too, the isolable yields remain reduced because by-product formation is still increased, which means that the reaction has a high conversion but only a low selectivity. With all other carbonates, the conversions and hence also the isolated yields remain incomplete in residence times achievable on the industrial scale (DE 3202690).

The invention is illustrated in the detail in the examples which follow.

EXAMPLE 1

In a 500 ml four-neck flask with stirrer, reflux condenser, internal thermometer and protective gas blanketing, 12.0 g (98.0 mmol) of 2,4-diaminotoluene, 9.42 g (98.0 mmol) of sodium isobutoxide and 68.3 g (392 mmol) of diisobutyl carbonate were weighed in successively under argon and immersed into an oil bath preheated to 125° C. After the mixture had been stirred at this temperature for 3 h, it was diluted with 200 ml of toluene and cooled to 50° C., and then 100 ml of water were metered in. On completion of phase separation, the organic upper phase was washed once with 100 ml of water. The aqueous phases were re-extracted twice with 100 ml each time of toluene and all organic phases were combined. 429 g of yellow solution were obtained, the bisurethane content of which was determined by means of HPLC to be 7.08% by weight (96%).

COMPARATIVE EXAMPLE 1

In a 500 ml four-neck flask with stirrer, reflux condenser, internal thermometer and protective gas blanketing, 12.1 g (98.7 mmol) of 2,4-diaminotoluene, 8.10 g (98.7 mmol) of sodium n-propoxide and 57.7 g (395 mmol) of di-n-propyl carbonate were weighed in successively under argon and immersed into an oil bath preheated to 125° C. After the mixture had been stirred at this temperature for 3 h, the mixture was worked up as described in example 1.399 g of yellow-brown solution were obtained, the bisurethane content of which was determined by means of HPLC to be 5.58% by weight (77%).

COMPARATIVE EXAMPLE 2

In a 500 ml four-neck flask with stirrer, reflux condenser, internal thermometer and protective gas blanketing, 12.1 g (98.7 mmol) of 2,4-diaminotoluene, 9.68 g (98.7 mmol) of sodium 2-methoxyethoxide and 70.4 g (395 mmol) of bis(2-methoxyethyl) carbonate were weighed in successively under argon and immersed into an oil bath preheated to 125° C. After the mixture had been stirred at this temperature for 3 h, the mixture was worked up as described in example 1.407 g of yellow-brown solution were obtained, the bisurethane content of which was determined by means of HPLC to be 6.64% by weight (84%).

COMPARATIVE EXAMPLE 3

In a 250 ml four-neck flask with stirrer, reflux condenser, internal thermometer and protective gas blanketing, 12.2 g (100 mmol) of 2,4-diaminotoluene, 2.07 g of 28% solution of sodium methoxide in methanol (corresponds to 10.7 mmol of sodium methoxide) and 121.4 g (600 mmol) of bis(3-methylbutyl) carbonate were weighed in successively under argon and immersed into an oil bath preheated to 80° C. The conversion was analyzed from time to time by means of thin-layer chromatography. Even after 140 h of reaction time at 80° C., distinct proportions of 2,4-diaminotoluene and the isomeric aminourethanes were still present. The bisurethane content determined by means of HPLC at this time was about 6.45% by weight (25%).

EXAMPLE 2

In a 500 ml four-neck flask with stirrer, reflux condenser, internal thermometer and protective gas blanketing, 11.9 g (97.1 mmol) of 2,4-diaminotoluene, 9.33 g (97.1 mmol) of sodium isobutoxide and 67.6 g (388 mmol) of diisobutyl carbonate were weighed in successively under argon and immersed into an oil bath preheated to 125° C. After the mixture had been stirred at this temperature for 2 h, the mixture was worked up as described in example 1.427 g of yellow solution were obtained, the bisurethane content of which was determined by means of HPLC to be 7.03% by weight (96%).

EXAMPLE 3

In a 500 ml four-neck flask with stirrer, reflux condenser, internal thermometer and protective gas blanketing, 11.8 g (96.8 mmol) of 2,4- and 2,6-diaminotoluene in a ratio of 80:20, 9.30 g (96.8 mmol) of sodium isobutoxide and 67.4 g (387 mmol) of diisobutyl carbonate were weighed in successively under argon and immersed into an oil bath preheated to 125° C. The content of bisurethanes in the reaction mixture was determined at periodic intervals by means of sampling and subsequent HPLC analysis. After 4 h, this was 32.2% by weight (91%).

EXAMPLE 4

In a 500 ml four-neck flask with stirrer, reflux condenser, internal thermometer and protective gas blanketing, 12.0 g (98.0 mmol) of 2,4- and 2,6-diaminotoluene in a ratio of 80:20, 14.1 g (147 mmol) of sodium isobutoxide and 68.1 g (391 mmol) of diisobutyl carbonate were weighed in successively under argon and immersed into an oil bath preheated to 125° C. The content of bisurethanes in the reaction mixture was determined at periodic intervals by means of sampling and subsequent HPLC analysis. After 3 h, this was 32.6% by weight (97%).

The invention claimed is:
1. A process for preparing a urethane, the process comprising:
reacting an aromatic amine with an organic dialkyl carbonate, wherein each alkyl radical of the organic dialkyl carbonate comprises from 4 to 18 carbon atoms and a primary alkyl chain of each alkyl radical is branched at a 2 position, and the reacting is in the presence of a base in a molar ratio of from 0.3 to less than 0.8, based on amino groups, and the reacting prepares a urethane at a yield of at least 91%.

2. The process of claim 1, wherein the aromatic amine comprises one amino group.

3. The process of claim 1, wherein the aromatic amine comprises two or more amino groups.

4. The process of claim 1, wherein an aromatic ring of the aromatic amine does not comprise a heteroatom.

5. The process of claim 1, wherein the aromatic amine is at least one aromatic amine selected from the group consisting of aniline; o-toluidine; m-toluidine; p-toluidine; o-chloroaniline; m-chloroaniline; p-chloroaniline; o-bromoaniline; m-bromoaniline; p-bromoaniline; o-trifluoromethylaniline; m-trifluoromethylaniline; p-trifluoromethylaniline; 2,4-, 2,6-, 3,4- or 3,5-dimethyl-, -dichloro-, -dibromo- or -diethylaniline or an isomer mixture thereof; p-tert-butylaniline; diaminotoluene (TDA); diaminodiphenylmethane (MDA); polyphenylenepolymethylenepolyamine; o-phenylenediamine; m-phenylenediamine; and p-phenylenediamine.

6. The process of claim 1, wherein the alkyl radical of the dialkyl carbonate is interrupted by an oxygen atom.

7. The process of claim 1, wherein the dialkyl carbonate derives from a primary alcohol.

8. The process of claim 1, wherein the dialkyl carbonate is at least one dialkyl carbonate selected from the group consisting of di(2-methylpropyl) carbonate, di(2-methoxypropyl) carbonate, di(2-ethoxypropyl) carbonate, di(2-methylbutyl) carbonate, di(2-ethylhexyl) carbonate, di(cyclopentylmethyl) carbonate, and di(cyclohexylmethyl) carbonate.

9. The process of claim 1,
wherein reacting the aromatic amine with the dialkyl carbonate comprises combining the dialkyl carbonate and the aromatic amine in a molar ratio of dialkyl carbonate to amino groups of from 1:1 to 6:1.

10. The process of claim 1, wherein the base is an alkoxide.

11. The process of claim 10, wherein the alkoxide is an alkoxide of an alkali metal or alkaline earth metal.

12. The process of claim 10, wherein a chain of the alkoxide has 1 to 18 carbon atoms.

13. The process of claim 12, wherein the chain of the alkoxide is an alkyl group interrupted by an oxygen atom.

14. The process of claim 10, wherein an alcohol of the alkoxide is identical to an alcohol of the dialkyl carbonate.

15. The process of claim 1,
wherein reacting the aromatic amine with the dialkyl carbonate yields a reaction product, and
the process further comprises reacting the reaction product with a protic compound, thereby obtaining a urethane mixture.

16. The process of claim 15, wherein the protic compound is water.

17. The process of claim 16, further comprising:
separating an aqueous base from the urethane mixture, thereby obtaining a urethane and an aqueous base,
converting the aqueous base to a corresponding nonaqueous base and recycling the nonaqueous base into reacting the aromatic amine with the organic dialkyl carbonate, and
isolating the urethane.

18. The process of claim 17, wherein the dialkyl carbonate is obtained in a process comprising transesterifying an alkylene carbonate with an alcohol.

19. The process of claim 17, further comprising:
cleaving the urethane to an isocyanate and alcohol after isolating the urethane.

20. A process for preparing a urethane, the process comprising:
reacting an aromatic amine with an organic dialkyl carbonate,
wherein each alkyl radical of the organic dialkyl carbonate comprises from 4 to 18 carbon atoms and a primary alkyl chain of each alkyl radical is branched at a 2 position, and
the reacting is in the presence of a base in a molar ratio of from 0.3 to 0.6, based on amino groups.

* * * * *